United States Patent
Enomoto

(10) Patent No.: US 9,469,604 B2
(45) Date of Patent: Oct. 18, 2016

(54) METHOD OF MANUFACTURING SULFONIUM SALT

(71) Applicant: TOYO GOSEI CO., LTD., Chiba (JP)

(72) Inventor: Satoshi Enomoto, Chiba (JP)

(73) Assignee: TOYO GOSEI CO., LTD., Chiba (JP)

( * ) Notice: Subject to any disclaimer, the term of this patent is extended or adjusted under 35 U.S.C. 154(b) by 0 days.

(21) Appl. No.: 14/847,950

(22) Filed: Sep. 8, 2015

(65) Prior Publication Data

US 2016/0068477 A1   Mar. 10, 2016

Related U.S. Application Data

(60) Provisional application No. 62/047,478, filed on Sep. 8, 2014.

(30) Foreign Application Priority Data

Aug. 20, 2015 (JP) .................. 2015-162810

(51) Int. Cl.
C07C 303/32 (2006.01)
C07C 381/12 (2006.01)
G03F 7/004 (2006.01)

(52) U.S. Cl.
CPC ........... *C07C 303/32* (2013.01); *C07C 381/12* (2013.01); *G03F 7/0045* (2013.01)

(58) Field of Classification Search
CPC .......................... C07C 381/12; C07C 303/32
See application file for complete search history.

(56) References Cited

U.S. PATENT DOCUMENTS 5,012,001 A * 4/1991 Crivello ............... C07D 333/76 568/1

FOREIGN PATENT DOCUMENTS

JP        61-100557 A      5/1986

OTHER PUBLICATIONS

Zaragoza Dorwald, Side Reactions in Organic Synthesis, 2005, WILEY-VCH Verlag GmbH & Co. KGaA, Weinheim, Preface. p. IX.*

* cited by examiner

*Primary Examiner* — Paul A Zucker
(74) *Attorney, Agent, or Firm* — Maier & Maier, PLLC

(57) ABSTRACT

Provided is a sulfonium salt manufacturing method which can reduce the production of a monosulfonium salt. A method of manufacturing a sulfonium salt includes preparing a first sulfonium salt containing a sulfonium cation and a first anion, preparing a second sulfonium salt by exchanging the first anion for a halide ion, and preparing a third sulfonium salt by exchanging the halide ion for a second anion.

19 Claims, 3 Drawing Sheets

METHOD OF MANUFACTURING SULFONIUM SALT

TECHNICAL FIELD

Some aspects of the present invention relate to a method of manufacturing a sulfonium salt which is useful as a photoacid generator.

BACKGROUND ART

Salts of triarylsulfonium and a fluorine-containing anion ($BF_4$, $PF_6$, $AsF_6$, $SbF_6$, etc.) have been known as polymerization initiators having a high photocationic polymerization initiation capability.

Among proposed sulfonium salt manufacturing methods, there is known, for example, a method including condensing a sulfide and a sulfoxide in the presence of at least one of an inorganic acid such as sulfuric acid and a strong organic acid such as methanesulfonic acid and subsequently exchanging an anion derived from the strong organic acid for a fluorine-containing anion (for example, see Japanese Unexamined Patent Application Publication No. 61-100557). In this method, there is produced a monosulfonium salt having one sulfonio group in one molecule, as well as a bissulfonium salt having two sulfonio groups in one molecule.

SUMMARY OF INVENTION

According to an investigation performed by the present inventor, a bissulfonium salt has higher water-solubility than a monosulfonium salt. For this reason, in the process of soaking a photoresist in water, such as an electrolytic plating process, it is preferred to add a monosulfonium salt as a sulfonium salt to the photoresist. In the traditional art, however, a bissulfonium salt is produced by a side reaction and therefore it is not easy to reduce the content thereof.

Some aspects of the present invention have been made in view of the foregoing, and an object thereof is to provide a sulfonium salt manufacturing method which can reduce the production of a bissulfonium salt.

Some aspects of the present invention provide a method of manufacturing a sulfonium salt including preparing a first sulfonium salt containing a sulfonium cation and a first anion, preparing a second sulfonium salt by exchanging the first anion for a halide ion, and preparing a third sulfonium salt by exchanging the halide ion for a second anion.

To reduce the production of a bissulfonium salt, the present inventor have investigated. As a result, the present inventor found that the production of a bissulfonium salt could be reduced by exchanging a first anion of a sulfonium salt for a halide ion and then exchanging the halide ion for a second anion rather than directly exchanging the first anion of the sulfonium salt for the second anion, and then completed the present invention. The sulfonium salt obtained by the method of one aspect of the present invention serves as a photoacid generator and can be used as a cation polymerization initiator by adding it to a photoresist. This photoacid generator may be added to a composition containing a polymer to be decomposed by an acid so that a polymer decomposition reaction is initiated by applying light. This photoacid generator may also be added to a composition containing a precursor which reacts with another substance in the presence of an acid so that a reaction is initiated by irradiating such composition with a light.

Various aspects of the present invention are described below. Any of the aspects below can be combined with each other.

Preferably, the sulfonium cation contains at least one aryl group.

Preferably, the first sulfonium salt is prepared by condensing a sulfoxide compound and an aryl compound in the presence of an acid.

Preferably, the sulfoxide compound is a diaryl sulfoxide compound which is optionally substituted.

Preferably, the aryl compound is a diaryl sulfide compound which is optionally substituted.

Preferably, the acid is sulfuric acid or sulfonic acid.

Preferably, the second sulfonium salt is prepared by causing a halide containing the halide ion to react with the first sulfonium salt.

Preferably, the third sulfonium salt is prepared by causing a metal salt containing the second anion to react with the second sulfonium salt.

Preferably, the second anion contains at least one fluorine atom.

Preferably, the second anion is one anion selected from the group consisting of $CF_3SO_3^-$, $CF_3CF_2CF_2CF_2SO_3^-$, $AsF_6^-$, $PF_6^-$, $SbF_6^-$, $BF_4^-$, and $B(C_6F_5)_4^-$.

DESCRIPTION OF EMBODIMENTS

Figure 1A:
FIGS. 1(a) to 1(e) illustrate an electrolytic plating process included in fabrication processes of a device such as integrated circuit (IC) using photoresist including a photoacid generator.

Now, an embodiment of one aspect of the present invention will be described. Various features described in the embodiment below can be combined with each other. Inventions are established for respective features.

1. Method of Manufacturing Sulfonium Salt

A method of manufacturing a sulfonium salt of an embodiment of an aspect of the present invention includes preparing a first sulfonium salt containing a sulfonium cation and a first anion, preparing a second sulfonium salt by exchanging the first anion for a halide ion, and preparing a third sulfonium salt by exchanging the halide ion for a second anion.

<First Sulfonium Salt Preparation Process>

This process is a process of preparing a first sulfonium salt containing a sulfonium cation and a first anion. The sulfonium cation is represented by Formula (1) below. The first anion serves as the counter anion of the sulfonium cation, as well as produce a weaker acid than the conjugate acid of the second anion.

[Formula 1]

(1)

where $R^1$ to $R^3$ may be the same or different; and are each a hydrogen atom, a hydrocarbon group which is optionally substituted by a substituent group, or a heterocyclic group which is optionally substituted by a substituent group; and two or three of $R^1$ to $R^3$ may be bonded together to form a ring.

Examples of the hydrocarbon group include alkyl groups such as methyl, ethyl, butyl, and octyl; cycloalkyl groups such as cyclopenthyl and cyclohexyl; and aryl groups such as phenyl, naphthyl, and anthryl. Examples of the heterocyclic group include aromatic heterocyclic groups such as pyridyl and furfuryl.

Examples of the substituent group include alkyl groups such as methyl and ethyl; aryl groups such as phenyl, naphthyl, and anthryl; alkyloxy groups such as methoxy; aryloxy groups such as phenoxy; alkylthio groups such as methylthio; arylthio groups such as phenylthio; acyl groups such as acetyl; aroyl groups such as benzoyl; acyloxy groups such as acetoxy; aroyloxy groups such as benzoyloxy; nitrile group; nitro group; hydroxy group; and halogen atoms.

The sulfonium cation is, for example, a sulfonium cation containing at least one aryl group, more specifically, a triarylsulfonium cation, even more specifically, a diphenyl [4-(phenylthio)phenyl]-sulfonium cation. The conjugate acid of the first anion is, for example, sulfonic acids, more specifically, alkyl sulfonic acids, even more specifically, C1 to C8 alkyl sulfonic acids, still more specifically, methanesulfonic acids.

The method of preparing the first sulfonium salt is not particularly limited. For example, the first sulfonium salt may be prepared by condensing a sulfoxide compound and an aryl compound in the presence of an acid. For example, the condensation reaction may be facilitated by adding the sulfoxide compound and aryl compound to a reaction solvent formed of an acid and stirring the mixture. In the first sulfonium salt thus prepared, an anion composed of the conjugate base of the above acid serve as the first anion of the first sulfonium salt. A mixture of a solvent and acid which do not inhibit the condensation reaction may be used as a reaction solvent.

The sulfoxide compound is represented by Formula (2) below.

[Formula 2]

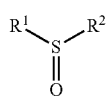

(2)

where $R^1$ and $R^2$ are defined as in Formula (1) and may be bonded together to form a ring.

Specific examples of the sulfoxide compound include dimethyl sulfoxide, methylethylsulfoxide, tetramethylenesulfoxide, diphenyl sulfoxide, dibenzothiophene-S-oxide, (4-methylphenyl)phenyl sulfoxide, 4,4'-dimethyldiphenylsulfoxide, 4,4'-dimethoxydiphenylsulfoxide, 4-methylthiodiphenylsulfoxide, (4-phenylthiophenyl)phenyl sulfoxide, 4,4'-dihydroxydiphenylsulfoxide, 4,4'-difluorodiphenylsulfoxide, 4,4'-dichlorodiphenylsulfoxide, 4,4'-dinitrodiphenylsulfoxide, 4-benzoyldiphenylsulfoxide, and 4,4'-carboxydiphenylsulfoxide. These sulfoxide compounds may be used alone or in combination.

Preferred sulfoxide compounds are diaryl sulfoxide compounds which is optionally substituted and, in particular, diphenylsulfoxide, dibenzothiophene-S-oxide, 4,4'-dimethyldiphenylsulfoxide, 4,4'-dimethoxydiphenylsulfoxide, 4,4'-dihydroxydiphenylsulfoxide, 4,4'-difluorodiphenylsulfoxide, and 4,4'-dichlorodiphenylsulfoxide.

The aryl compound is a compound having a function of introducing $R^3$ in Formula (1). In order to form a first sulfonium salt by a condensation reaction between the sulfoxide compound and aryl compound, the aryl compound preferably has at least one hydrogen atom which is desorbed when condensation is performed. If the aryl compound has two or more hydrogen atoms which are desorbed when condensation is performed, a bissulfonium salt is more likely to be produced. Accordingly, the technical superiority of one aspect of the present invention becomes remarkable.

Examples of the aryl compound include monocyclic or condensed polycyclic aryl compounds being unsubstituted, such as benzene, naphthalene, anthracene, phenanthrene, naphthacene, and pyrene; aryl compounds substituted by an alkyl group, such as toluene, cumene, tert-butylbenzene, xylene, ethylbenzene, dodecylbenzene, 1-methylnaphthalene, and 1H-indene; aryl compounds substituted by an aryl group, such as biphenyl, biphenylene, 1,2'-binaphthyl, and 2-phenylnaphthalene; aryl compounds substituted by an alkoxy group which is optionally substituted, such as anisole, ethoxybenzene, 1-methoxynaphthalene, benzylphenylether, and benzofuran; aryl compounds substituted by an aryloxy group which is optionally substituted, such as diphenylether, 2-ethoxynaphthalene, 4-phenoxyphenol, and xanthene; aryl compounds substituted by an alkylsulfonyl group, such as methylphenylsulfone; aryl compounds substituted by an arylsulfonyl group, such as diphenylsulfone; aryl compounds substituted by an alkylthio group which is optionally substituted, such as thioanisole, ethylthiobenzene, benzothiophene, benzyl phenyl sulfide, and phenacyl phenyl sulfide; and aryl compounds substituted by an arylthio group which is optionally substituted (i.e., diaryl sulfide compounds), such as diphenyl sulfide, dibenzothiophene, (2-methylphenyl)phenyl sulfide, (4-methylphenyl)phenyl sulfide, 2,2'-ditolyl sulfide, 2,3'-ditolyl sulfide, 2-phenylthionaphthalene, 9-phenylthioanthracene, (3-chlorophenyl) phenyl sulfide, (4-chlorophenyl)phenyl sulfide, 3,3'-dichlorodiphenyl sulfide, (3-bromophenyl)phenyl sulfide, 2,2'-dibromodiphenyl sulfide, 3,3'-dibromodiphenyl sulfide, (2-methoxyphenyl)phenyl sulfide, phenoxathiin, thioxanthone, 2-isopropylthioxanthone, 2-methoxythioxanthone, 4,4'-diphenyl thiobenzophenone, 4,4'-diphenylthiodiphenylether, 4,4'-diphenylthiobiphenyl, (4-phenylthiophenyl)phenyl sulfide, (4-benzoylphenyl)phenyl sulfide, (2-chloro-4-benzoylphenyl)phenyl sulfide, and (2-methylthio benzoylphenyl)phenyl sulfide.

The acid facilitates the condensation reaction between the sulfoxide compound and aryl compound, as well as serves as a reaction solvent for the condensation reaction. Available acids include: organic acids such as sulfonic acid and carboxylic acid; and inorganic acids such as sulfuric acid.

Examples of the sulfonic acid include alkyl sulfonic acid and aromatic sulfonic acid. Among these, alkyl sulfonic acid is preferable, and C1 to C8 alkyl sulfonic acid is more preferable. Preferred specific examples include methanesulfonic acid, ethanesulfonic acid, propanesulfonic acid, butanesulfonic acid, pentanesulfonic acid, and octanesulfonic acid.

Examples of the carboxylic acid include alkyl carboxylic acids and aromatic carboxylic acids. Among these, alkyl carboxylic acids are preferable, and C1 to C8 alkyl carboxylic acid is more preferable. Preferred specific examples include acetic acid, propionic acid, butanoic acid, pentanoic acid, and hexanoic acid.

Preferably, a dehydrating agent is added to the reaction solvent. Thus, water produced in the condensation reaction is removed from the reaction system, so that the condensation reaction is facilitated. Examples of the dehydrating agent include: inorganic oxides such as phosphorus pentaoxide; inorganic acids such as polyphosphoric acid; and organic acid anhydrides such as acetic anhydride, propionic anhydride and phthalic anhydride. These dehydrating agents may be used alone or in combination. Among these, organic acid anhydrides, particularly acetic anhydride, are preferred.

<Second Sulfonium Salt Preparation Process>

This process is a process of preparing a second sulfonium salt by exchanging the first anion of the first sulfonium salt for a halide ion.

The second sulfonium salt can be prepared, for example, by causing a halide containing the halide ion to react with the first sulfonium salt. This reaction may be caused, for example, by adding the first sulfonium salt and halide to a solvent forming an aqueous layer and an organic layer, and by stirring the mixture. If the solubility of the second sulfonium salt composed of the sulfonium cation and the halide ion in the organic layer is higher than the solubility of a salt composed of the counter cation of the halide and the first anion in the organic layer, the second sulfonium salt can be selectively captured into the organic layer by stirring the first sulfonium salt and halide in the solvent.

For example, dichloromethane or the like may be used as an organic solvent which forms an organic layer and in which the second sulfonium salt can be dissolved.

Examples of the halide such as fluoride, chloride, bromide, iodide include hydrogen halides and salts of halogenated alkali metals such as lithium, sodium, potassium, etc. Examples of the hydrogen halides include hydrogen chloride and hydrobromic acid, and examples of the halogenated alkali metal salts include sodium chloride and sodium bromide.

<Third Sulfonium Salt Preparation Process>

This process is a process of preparing a third sulfonium salt by exchanging the halide ion of the second sulfonium salt for a second anion.

Preferably, the conjugate acid of the second anion is stronger than that of the first anion. A sulfonium salt prepared by exchanging the first anion of the sulfonium salt for such a second anion generates a stronger acid as a photoacid generator.

Examples of the conjugate acids of the second anion include inorganic acids and organic acids. Examples of the inorganic acids include hexafluoroantimonic acid, hexafluoroarsenic acid, hexafluorophosphoric acid, pentafluorohydroxoantimonic acid, tetrafluoroboric acid, trifluorotristrifluoro methyl phosphoric acid, trifluorotrispentafluoroethyl phosphoric acid, trifluorotrisheptafluoropropyl phosphoric acid, tetrakis(pentafluorophenyl)boric acid, tetrakis(trifluoromethylphenyl)boric acid, trifluoro(pentafluorophenyl)boric acid, tetrakis(difluorophenyl)boric acid, and difluorobis(pentafluorophenyl)boric acid. Examples of the organic acids include C1 to C8 alkyl sulfonic acids and such acids where some or all hydrogen atoms of an alkyl group are substituted by fluorine atoms. Examples of the alkyl sulfonic acids include methanesulfonic acid, ethanesulfonic acid, propanesulfonic acid, butanesulfonic acid, pentanesulfonic acid, and octanesulfonic acid.

Further, the second anion preferably contains at least one fluorine atom, more preferably is composed of one of $CF_3SO_3^-$, $CF_3CF_2CF_2CF_2SO_3^-$, $AsF_6^-$, $PF_6^-$, $SbF_6^-$, $BF_4^-$, and $B(C_6F_5)_4^-$.

The third sulfonium salt can be prepared, for example, by causing a metal salt containing the second anion to react with the second sulfonium salt. This reaction can be caused, for example, by adding the second sulfonium salt and metal salt to a solvent forming an aqueous layer and an organic layer, and by stirring the mixture. If the solubility of the third sulfonium salt composed of the sulfonium cation and second anion in the organic layer is higher than the solubility of a salt composed of the counter cation of the second anion and the halide ion in the organic layer, the third sulfonium salt can be selectively captured into the organic layer by stirring the second sulfonium salt and metal salt in the solvent.

For example, dichloromethane or the like may be used as an organic solvent which forms an organic layer and in which the third sulfonium salt can be dissolved. Preferably, the metal salt of the second anion is an alkali metal salt, such as a lithium salt, sodium salt, or potassium salt.

Through the above processes, the sulfonium salt of the present embodiment is manufactured. The present embodiment is characterized in that instead of directly exchanging the first anion of the sulfonium salt for the second anion, the first anion is exchanged for the halide ion and then the halide ion is exchanged for the second anion. By manufacturing the sulfonium salt through these processes, it is possible to reduce the production of a bissulfonium salt. This is demonstrated in Example to be discussed later.

A bissulfonium salt has higher water-solubility than a monosulfonium salt. For this reason, in the process of soaking a photoresist in water, such as an electrolytic plating process, the sulfonium salt of the present embodiment, which contains a bissulfonium salt in a lower content, can be added as a suitable photoacid generator to the photoresist.

2. Electrolytic Plating Process

Now, there will be described an electrolytic plating process which uses a photoresist containing the sulfonium salt manufactured by the above method as a photoacid generator. The photoresist contains polymers and the above sulfonium salt. The polymers include, for example, polymers A and B below. The sulfonium salt is, for example, diphenyl[4-(phenylthio)phenyl]-sulfonium nonaflate prepared in Example to be discussed later. The electrolytic plating process is included in the manufacturing processes of a device such as an integrated circuit (IC). The electrolytic plating process includes forming a conducting part in a through-hole formed in a photolithography process.

[Formula 3]

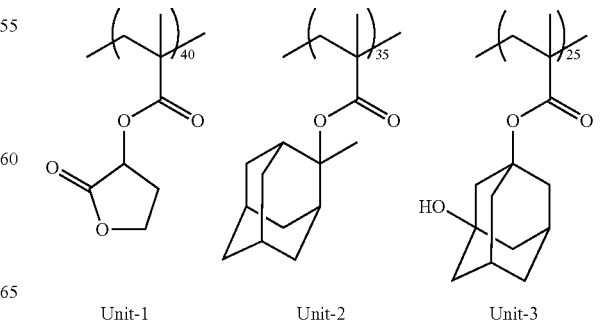

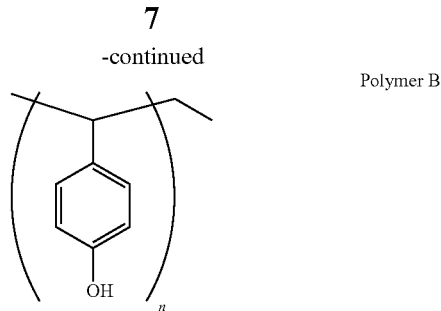
Polymer B

Figure 1B:
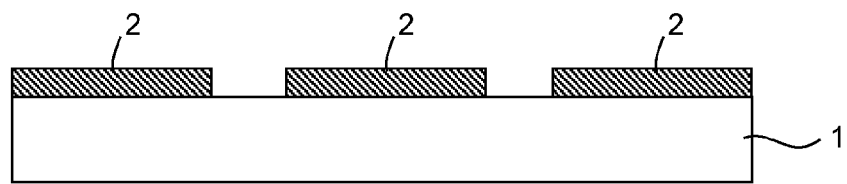

First, as illustrated in FIG. 1(a), Core Substrate 1 is prepared. Then, as illustrated in FIG. 1(b), a patterned Conductor Layer 2 is formed on the surface of Core Substrate 1.

Figure 1C:
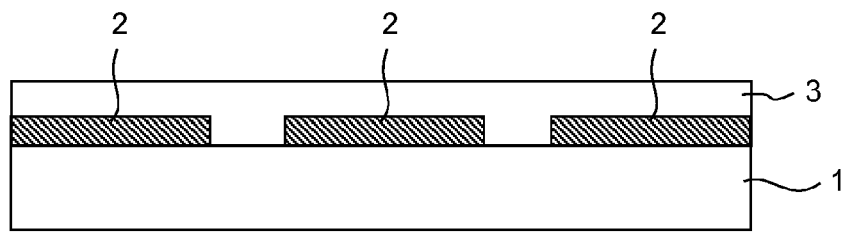

Then, as illustrated in FIG. 1(c), a thermal curing resin is applied such that the thermal curing resin covers Conductor Layer 2 and Core Substrate 1. Solder Resist Layer 3 of which thickness is around 20 μm is obtained by thermally curing the thermal curing resin.

Figure 1D:
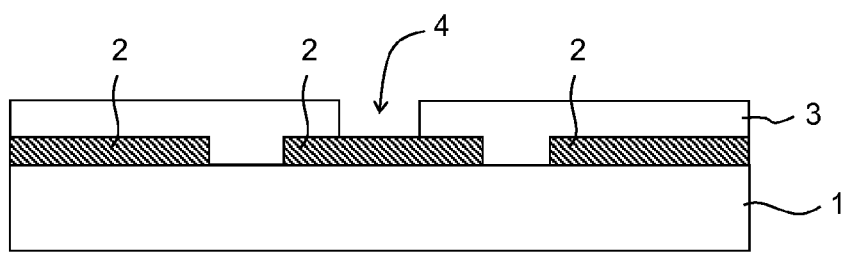

Then, as illustrated in FIG. 1(d), First Through-Hole 4 is formed by an irradiation of Solder Resist Layer 3 with a laser light such that a portion of Conductor Layer 2 is exposed on the surface. Smear remaining inside First Through-Hole 4 is removed by a desmear treatment.

Figure 1E:
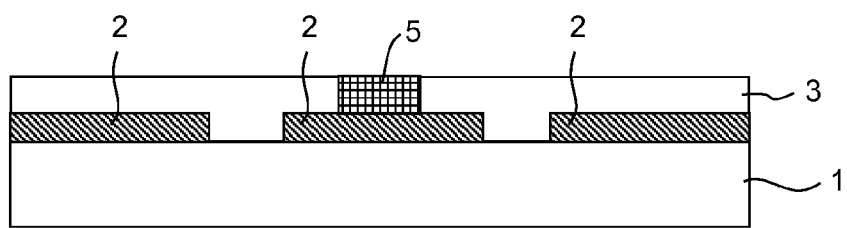

Then, as illustrated in FIG. 1(e), First Conducting Part 5 is formed by soaking in a solution containing a nickel salt, copper sulfate, sodium hydroxide, a complexing agent and a chelating agent the member which has been obtained by the above-mentioned processes in which Through-Hole 4 has been formed.

Figure 2A:
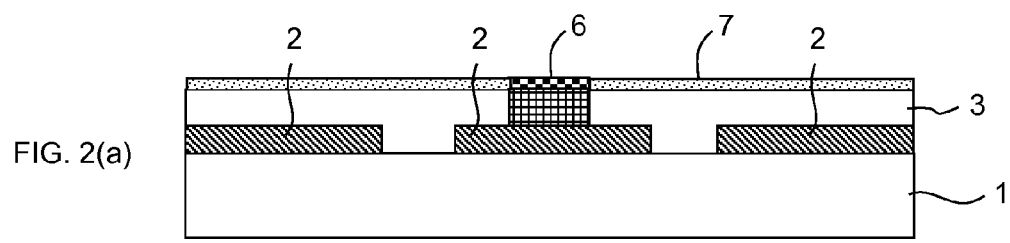
FIGS. 2(a) to 2(c) illustrate an electrolytic plating process following FIG. 1(e).

Then, as illustrated in FIG. 2(a), Interposition Layer 6 and Electroless Plating Layer 7 are formed by an electroless plating process.

Figure 2B:
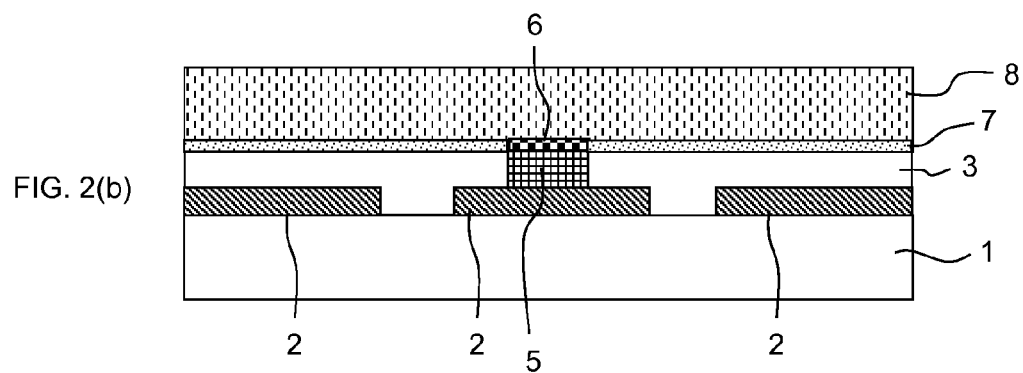

Then, as illustrated in FIG. 2(b), Photoresist Layer 8 of which thickness is equal to or greater than 20 μm is formed such that Photoresist Layer 8 covers Interposition Layer 6 and Electroless Plating Layer 7. The thickness of Photoresist Layer 8 is preferably 30 μm or more, and more preferably 40 μm or more.

Figure 2C:
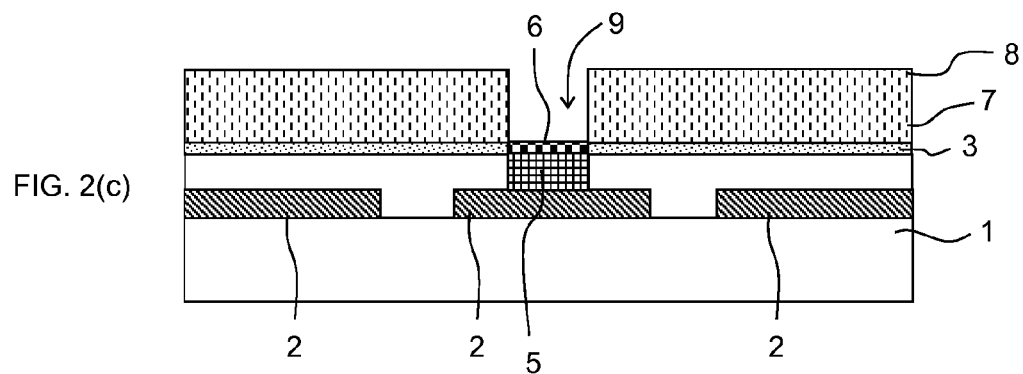

Then, as illustrated in FIG. 2(c), Second Through-Hole 9 is formed by a photolithography process such that Interposition Layer 6 is exposed on the surface. Specifically, Second Through-Hole 9 is formed by exposing and curing Photoresist Layer 8 in a state in which a portion corresponding to Second Through-Hole 9 is covered by a shielding pattern and then melting the portion covered by the shielding pattern. For example, when Photoresist Layer 8 is exposed to light having a wavelength of 365 nm, the photoacid generator absorbs the light and thus is decomposed, producing the conjugate acids of the second anion. These acids initiate the cationic polymerization between the polymers A and B, curing Photoresist Layer 8.

Figure 3A:
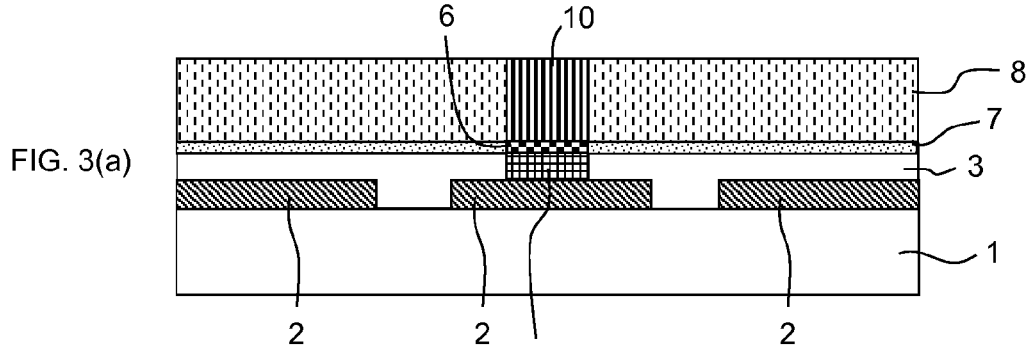
FIGS. 3(a) to 3(c) illustrate an electrolytic plating process following FIG. 2(c).

Then, as illustrated in FIG. 3(a), Second Conducting Part 10 is formed by an electrolytic plating process in which Electroless Plating Layer 7 is used as an electrode through which voltage is applied. In this electrolytic plating process, Photoresist Layer 8 is soaked in an electrolyte solution using water as a solvent. At this time, if the sulfonium salt contains water-soluble components in a low content, the contamination of the plating solution is prevented, and acids are less likely to occur in the plating solution. As a result, there is obtained an advantage that the contamination of the equipment or working environment is reduced. Since the sulfonium salt of the present embodiment contains a bissulfonium salt, which is water-soluble, in a very low content, the above advantage is obtained.

Figure 3B:
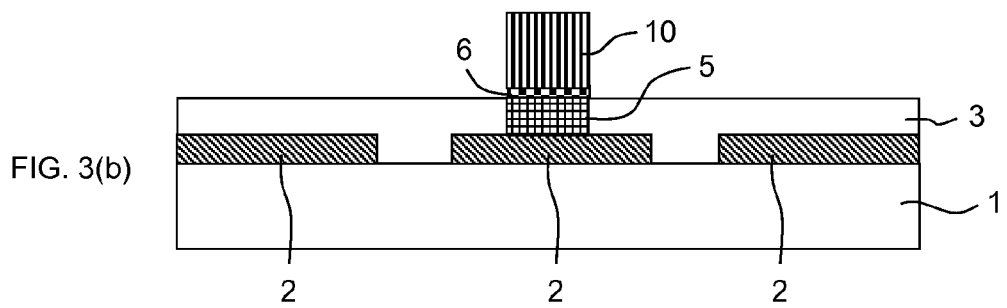

Then, as illustrated in FIG. 3(b), Photoresist Layer 8 is removed by soaking in a stripping solution containing an amine the member which has been obtained by the above-mentioned processes in which Second Conducting Part 10 has been formed.

Figure 3C:
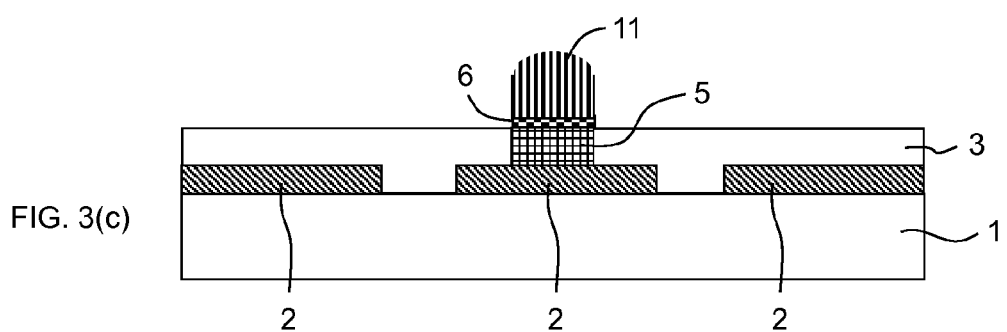

Then, as illustrated in FIG. 3(c), the member which has been obtained by the above-mentioned processes is subjected to a reflow treatment in a reflow furnace which is set at a temperature greater than a melting point of at least one constituent of Second Conducting Part 10. By this treatment, Conducting Post 11 is formed.

The method of fabrication of a conducting part or conducting post explained above can be applied to a fabrication of devices such as electronic device including IC chip and electro-optical device including display devices.

Especially, the method of fabrication of a conducting part or conducting post explained above is suitable for high-density packaging.

Example

Diphenyl[4-(phenylthio)phenyl]-sulfonium nonaflate (PSDPS-Nf) was synthesized according to an experimental procedure described below and by direct salt exchange method (method A) and by indirect salt exchange method (method B) respectively, and the contents of bissulfonium salts in the products are compared.

(1) Synthesis of PSDPS-Nf by Direct Salt Exchange Method (Method A)

10.0 g of diphenylsulfoxide and 11.1 g of diphenyl sulfide were dissolved in 26.5 g of methane sulfonic acid. 3.16 g of phosphorus oxide was added to the methane sulfonic acid solution containing diphenylsulfoxide and diphenyl sulfide over 10 minutes. The mixture was stirred at 25 degrees Celsius for 3 hours. Since then, the mixture was cooled to 5 degrees Celsius and it was further stirred for 10 minutes after addition of 60.0 g of water. Then the solution was washed with 20 g of ethyl acetate, and water layer was collected. This water layer contains diphenyl[4-(phenylthio)phenyl]-sulfonium methane sulfonate produced by condensing diphenylsulfoxide and diphenyl sulfide.

Thereafter, 17.5 g of potassium nonaflate (potassium nonafluorobutanesulfonate) and 40 g of dichloromethane were added to the above aqueous solution. The mixture was stirred at 25 degrees Celsius for 1 hour to extract PSDPS-Nf in a dichloromethane layer, and the dichloromethane layer was collected. Then the dichloromethane solution was washed with water four times, and dichloromethane was distilled away. Thereby 27.1 g of PSDPS-Nf was obtained. Thereafter, purity of product was measured by means of internal reference method using HPLC. As the result, it was observed that the product contained 2.4% of bis-[4-(diphenyl sulfonio)phenyl]-sulfide bis-nonaflate as an impurity.

The structural formula of PSDPS-Nf is shown below.

[Formula 4]

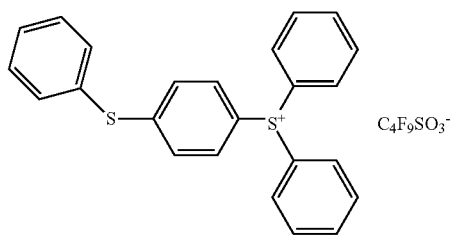

(4)

(2) Synthesis of diphenyl[4-(phenylthio)phenyl]-sulfonium bromide (PSDPS-Br)

20.0 g of diphenylsulfoxide and 22.1 g of diphenyl sulfide were dissolved in 57.0 g of methane sulfonic acid. 6.32 g of phosphorus oxide was added to the methane sulfonic acid solution containing diphenylsulfoxide and diphenyl sulfide over 10 minutes. The mixture was stirred at 25 degrees Celsius for 3 hours. Since then, the mixture was cooled to 5 degrees Celsius and it was further stirred for 10 minutes after addition of 120.0 g of water. Then the solution was washed with 40 g of ethyl acetate, and water layer was collected. This water layer contains diphenyl[4-(phenylthio)phenyl]-sulfonium methane sulfonate produced by condensing diphenylsulfoxide and diphenyl sulfide.

Thereafter, 16.67 g of 48% hydrogen bromide aqueous solution and 180 g of dichloromethane were added to the above aqueous solution. The mixture was stirred at 25 degrees Celsius for 1 hour to extract PSDPS-Br in a dichloromethane layer, and the dichloromethane layer was collected. Then the dichloromethane solution was washed with water twice and dichloromethane was distilled away. Thereby 48.2 g of PSDPS-Br was obtained.

(3) Synthesis of PSDPS-Nf by Indirect Salt Exchange Method (Method B)

20.0 g of PSDPS-Br obtained in the above (2) and 15.7 g of potassium nonaflate were added to the two layered solvent which consisted of 40 g of water and 80 g of dichloromethane. The mixture was stirred at 25 degrees Celsius for 1 hour to extract PSDPS-Nf in a dichloromethane layer, and the dichloromethane layer was collected. Then the dichloromethane solution was washed with water twice and dichloromethane was distilled away. Thereby 26.3 g of PSDPS-Nf was obtained, and purity of product was measured by means of internal reference method using HPLC. As the result, it was observed that the product contained 0.2% of bis-[4-(diphenyl sulfonio)phenyl]}-sulfide bis-nonaflate as an impurity.

(4) Experimental Procedure of Water Solubility Measurement 0.1 g of PSDPS-Nf was added to 10.0 g of water. The mixture was stirred at 80 degrees Celsius for 1 hour. Since then, the mixture was cooled to 25 degrees Celsius and it was further stirred for 10 minutes after addition of 0.02 g of sodium benzoate as an internal standard material. Then the mixture was filtered, and filtrate was collected. Thereafter, the water solubility of PSDPS-Nf was measured by means of internal reference method using HPLC.

The result is shown in Table 1. Table 1 shows the water solubility in wt % of each of synthesis methods A and B.

TABLE 1

| Evaluation sample | Synthesis method of PSDPS-Nf | Water solubility (wt %) |
|---|---|---|
| 1 | method A | 1.8 |
| 2 | method B | 0.1 |

Evaluation Sample 1 which is synthesized by method A shows higher water solubility than Evaluation Sample 2 which is synthesized by method B. This indicates that bis-[4-(diphenyl sulfonio)phenyl]-sulfide bis-nonaflate is mainly water soluble component in the Evaluation Samples. In other words, dicationic structure is eluted easier than monocationic structure to water. The less water solubility of the organic salt containing the monocation is more suitable for plating process which includes a process applied to formation of conducting part such as Cu pillar structure by photolithography patterning process.

What is claimed is:
1. A method of manufacturing a sulfonium salt, comprising:
   preparing a first sulfonium salt containing a sulfonium cation and a first anion;
   preparing a second sulfonium salt by exchanging the first anion for a halide ion; and
   preparing a third sulfonium salt by exchanging the halide ion for a second anion;
   wherein the first sulfonium salt is prepared by condensing a sulfoxide compound and an aryl compound in the presence of an acid;
   the sulfoxide compound is selected from the group consisting of dimethyl sulfoxide, methylethylsulfoxide, tetramethylenesulfoxide, diphenyl sulfoxide, dibenzothiophene-S-oxide, (4-methylphenyl)phenyl sulfoxide, 4,4'-dimethyldiphenylsulfoxide, 4,4'-dimethoxydiphenylsulfoxide, 4-methylthiodiphenylsulfoxide, (4-phenylthiophenyl)phenyl sulfoxide, 4,4'-dihydroxydiphenylsulfoxide, 4,4'-difluorodiphenylsulfoxide, 4,4'-dichlorodiphenylsulfoxide, 4,4'-dinitrodiphenylsulfoxide, 4-benzoyldiphenylsulfoxide, and 4,4'-carboxydiphenylsulfoxide; and
   the aryl compound is selected from the group consisting of benzene, naphthalene, anthracene, phenanthrene, naphthacene, pyrene, toluene, cumene, tert-butylbenzene, xylene, ethylbenzene, dodecylbenzene, 1-methylnaphthalene, 1H-indene, biphenyl, biphenylene, 1,2'-binaphthyl, 2-phenylnaphthalene, anisole, ethoxybenzene, 1-methoxynaphthalene, benzylphenylether, benzofuran, diphenylether, 2-ethoxynaphthalene, 4-phenoxyphenol, xanthene, methylphenylsulfone, diphenylsulfone, thioanisole, ethylthiobenzene, benzothiophene, benzyl phenyl sulfide, phenacyl phenyl sulfide, diphenyl sulfide, dibenzothiophene, 2-methylphenyl)phenyl sulfide, (4-methylphenyl)phenyl sulfide, 2,2'-ditolyl sulfide, 2,3'-ditolyl sulfide, 2-phenylthionaphthalene, 9-phenylthioanthracene, (3-chlorophenyl)phenyl sulfide, (4-chlorophenyl)phenyl sulfide, 3,3'-dichlorodiphenyl sulfide, (3-bromophenyl)phenyl sulfide, 2,2'-dibromodiphenyl sulfide, 3,3'-dibromodiphenyl sulfide, (2-methoxyphenyl)phenyl sulfide, phenoxathiin, thioxanthone, 2-isopropylthioxanthone, 2-methoxythioxanthone, 4,4'-diphenyl thiobenzophenone, 4,4'-diphenylthiodiphenylether, 4,4'-diphenylthiobiphenyl, (4-phenylthiophenyl)phenyl sulfide, (4-benzoylphenyl)phenyl sul- fide, (2-chloro-4-benzoylphenyl)phenyl sulfide, and (2-methylthio benzoylphenyl)phenyl sulfide.

2. The method of claim 1, wherein the sulfonium cation contains at least one aryl group.

3. The method of claim 1, wherein: the sulfoxide compound is a diaryl sulfoxide compound; and the diaryl sulfoxide compound is optionally substituted.

4. The method of claim 1, wherein: the aryl compound is a diaryl sulfide compound; and the diaryl sulfide compound is optionally substituted.

5. The method of claim 1, wherein the acid is sulfuric acid or a sulfonic acid compound.

6. The method of claim 1, wherein the second sulfonium salt is prepared by causing a halide containing the halide ion to react with the first sulfonium salt.

7. The method of claim 1, wherein the third sulfonium salt is prepared by causing a metal salt containing the second anion to react with the second sulfonium salt.

8. The method of claim 1, wherein the second anion contains at least one fluorine atom.

9. The method of claim 1, wherein the second anion is one anion selected from the group consisting of $CF_3SO_3^-$, $CF_3CF_2CF_2CF_2SO_3^-$, $AsF_6^-$, $PF_6^-$, $SbF_6^-$, $BF_4^-$, and $B(C_6F_5)_4^-$.

10. The method of claim 3, wherein the aryl compound is a diaryl sulfide compound; and the diaryl sulfide compound is optionally substituted.

11. The method of claim 3, wherein the acid is sulfuric acid or a sulfonic acid compound.

12. The method of claim 4, wherein the acid is sulfuric acid or a sulfonic acid compound.

13. The method of claim 2, wherein the second sulfonium salt is prepared by causing a halide containing the halide ion to react with the first sulfonium salt.

14. The method of claim 1, wherein the second sulfonium salt is prepared by causing a halide containing the halide ion to react with the first sulfonium salt.

15. The method of claim 3, wherein the second sulfonium salt is prepared by causing a halide containing the halide ion to react with the first sulfonium salt.

16. The method of claim 4, wherein the second sulfonium salt is prepared by causing a halide containing the halide ion to react with the first sulfonium salt.

17. The method of claim 5, wherein the second sulfonium salt is prepared by causing a halide containing the halide ion to react with the first sulfonium salt.

18. The method of claim 2, wherein the third sulfonium salt is prepared by causing a metal salt containing the second anion to react with the second sulfonium salt.

19. A method of manufacturing a device, comprising a process of an electrolytic plating using a photoresist containing the sulfonium salt manufactured by the method of claim 1.

* * * * *